US 6,727,086 B2

(12) United States Patent
Bathe et al.

(10) Patent No.: US 6,727,086 B2
(45) Date of Patent: Apr. 27, 2004

(54) NUCLEOTIDE SEQUENCES WHICH CODE FOR THE SIGH GENE

(75) Inventors: Brigitte Bathe, Salzkotten (DE); Indra Schröder, Steinhagen (DE); Mechthild Rieping, Bielefeld (DE); Achim Marx, Bielefeld (DE); Mike Farwick, Bielefeld (DE); Walter Pfefferle, Halle (DE); Thomas Hermann, Bielefeld (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/942,936

(22) Filed: Aug. 31, 2001

(65) Prior Publication Data

US 2002/0106756 A1 Aug. 8, 2002

(30) Foreign Application Priority Data

Sep. 2, 2000 (DE) .......................... 100 43 333
Jul. 10, 2001 (DE) .......................... 101 33 427

(51) Int. Cl.⁷ ................................ C12N 1/20
(52) U.S. Cl. .................. 435/252.32; 435/252.3; 435/320.1; 536/23.1; 536/23.2
(58) Field of Search ................ 435/252.3, 252.32, 435/320.1; 536/23.1, 23.2

(56) References Cited

U.S. PATENT DOCUMENTS 6,027,920 A    2/2000 Joliff et al.

FOREIGN PATENT DOCUMENTS

EP    0 864 654 A1    9/1998

OTHER PUBLICATIONS

Cole S T et al., "Deciphering the biology of Mycobacterium tuberculosis from the complete genome sequence.", vol. 393, No. 6685, Jun. 11, 1998, pp. 537–544.
Oguiza Jose A et al., "Multiple sigma factor genes in Brevibacterium lactofermentum: Characterization of sigA and sigB", vol. 178, No. 2, 1996, pp. 550–553.
Patent Abstracts of Japan, vol. 1996, No. 11, Nov. 29, 1996 & JP 08 173162, Jul. 9, 1996.

*Primary Examiner*—Ponnathapu Achutamurthy
*Assistant Examiner*—Christian L. Fronda
(74) *Attorney, Agent, or Firm*—Smith, Gambrell & Russell

(57) ABSTRACT

The invention relates to an isolated polynucleotide having a polynucleotide sequence which codes for the sigH gene, and a host-vector system having a coryneform host bacterium in which the sigH gene is present in attenuated form and a vector which carries at least the sigH gene according to SEQ ID No 1, and the use of polynucleotides which comprise the sequences according to the invention as hybridization probes.

18 Claims, 2 Drawing Sheets

Figure 1: Map of the plasmid pEC-XK99E
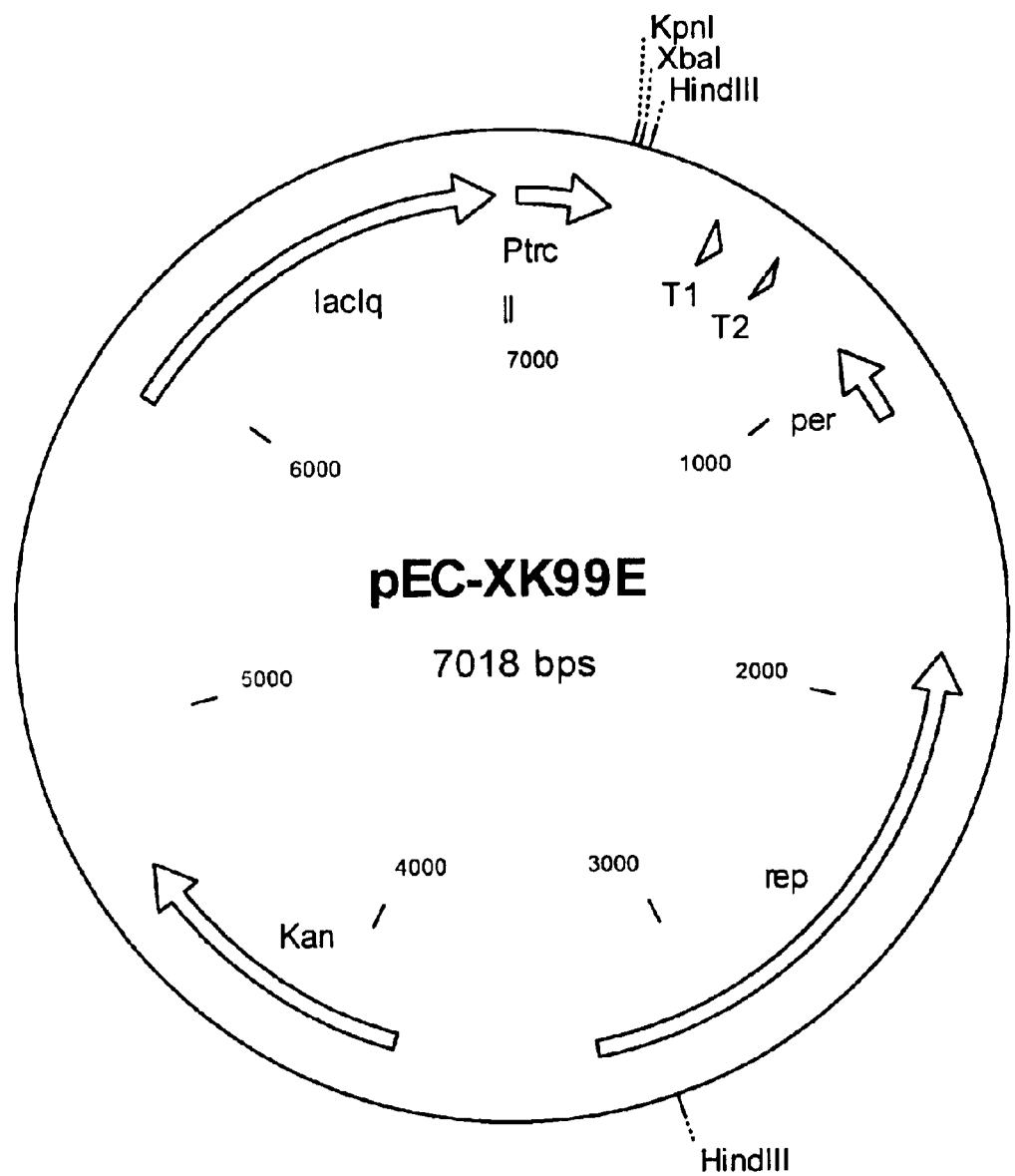

Figure 2: Plasmid pEC-XK99EsigHa1ex
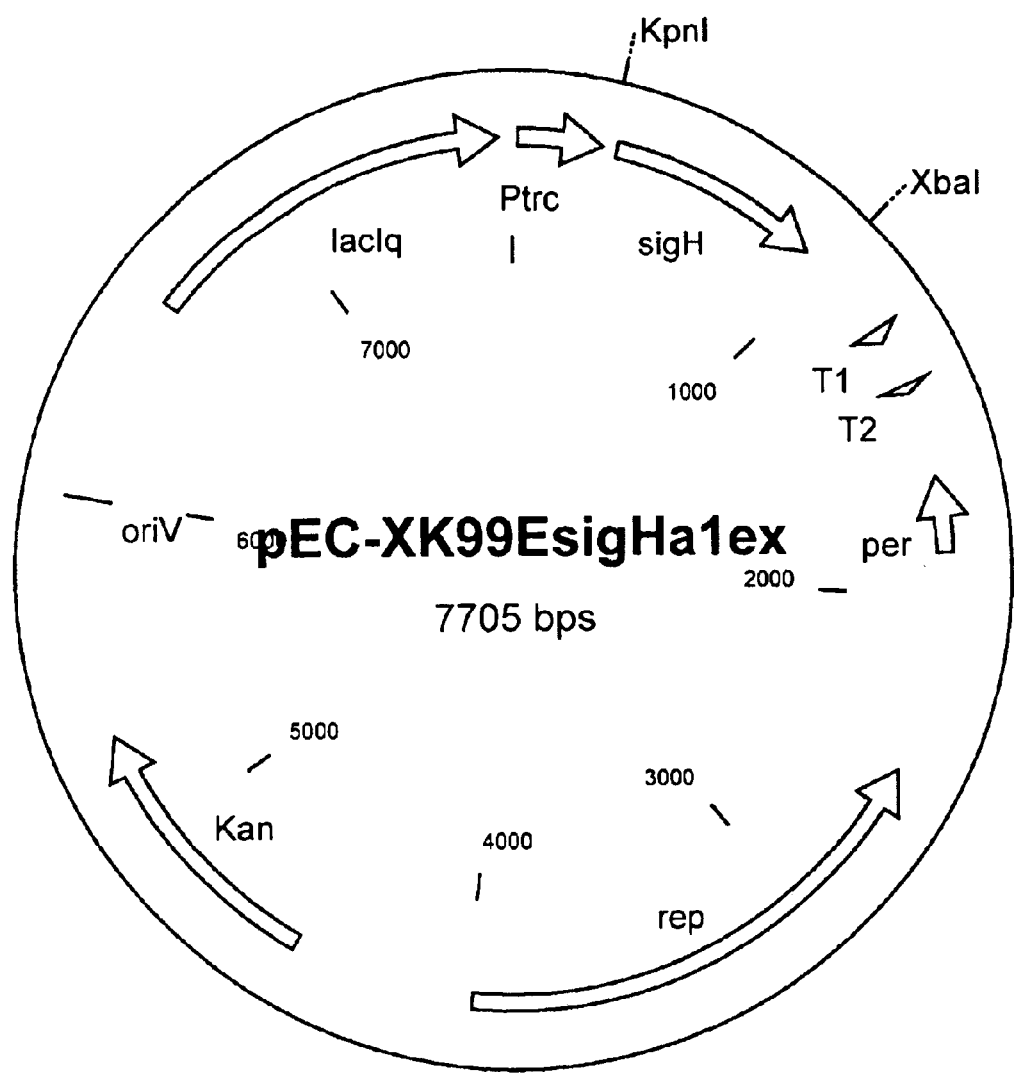

SEQUENCE LISTING

<160> NUMBER OF SEQ ID NOS: 4

<210> SEQ ID NO 1
<211> LENGTH: 1148
<212> TYPE: DNA
<213> ORGANISM: Corynebacterium glutamicum

```
<220> FEATURE:
<221> NAME/KEY: CDS
<222> LOCATION: (302)..(919)
<223> OTHER INFORMATION:

<400> SEQUENCE: 1
ttgttgatgg ctgtggctaa atcatcgtca tctttggggc gtaatcgatg ccaaaatgcg      60
aggtcacggc gattagtctc aacaatttcg gtgcttaaag gatcctgcgg attattgacg     120
gtgaagtaga acattgtttc ccctagatt  tgaagtggta catatgttct aactgatgtg     180
gtggacacgg gggggtagag taaagtctaa gcaacagctc acgtggcttt acagctaccc     240
ccgaaaggtc tgtttttat  cggaagtaga atagtcaaca cgcattttcg aaaggggcca     300 c atg gct gaa aac cga acc ggc aca gtc gat gga gac gcg ttg gct gcc     349
  Met Ala Glu Asn Arg Thr Gly Thr Val Asp Gly Asp Ala Leu Ala Ala
  1               5                  10                  15 cgc ttt gaa gag gag gca ctg cca ctc ctt gac cag ctc tat ggc ggt       397
Arg Phe Glu Glu Glu Ala Leu Pro Leu Leu Asp Gln Leu Tyr Gly Gly
            20                  25                  30 gct ctg cgc atg act aga aat ccc gca gat gcg gaa gat ctc gtg caa       445
Ala Leu Arg Met Thr Arg Asn Pro Ala Asp Ala Glu Asp Leu Val Gln
        35                  40                  45 gac acc tat atc aag gcg tac cag gcg ttc gcg agc ttc aaa cca ggc       493
Asp Thr Tyr Ile Lys Ala Tyr Gln Ala Phe Ala Ser Phe Lys Pro Gly
    50                  55                  60 acc aac ctg aag gct tgg ctc tat cgg atc atg acg aat acc tac atc       541
Thr Asn Leu Lys Ala Trp Leu Tyr Arg Ile Met Thr Asn Thr Tyr Ile
65                  70                  75                  80 aac atg tac cga aag aaa cag agg cag cca tcg caa acc tct gcc gat       589
Asn Met Tyr Arg Lys Lys Gln Arg Gln Pro Ser Gln Thr Ser Ala Asp
                85                  90                  95 gag atc act gac tac cag ctc gtt gaa tct caa tcg cat acc tca aca       637
Glu Ile Thr Asp Tyr Gln Leu Val Glu Ser Gln Ser His Thr Ser Thr
            100                 105                 110 ggg ctg gaa tcc gcc gag gtt gag gct ctg aaa aat ctg cca gac gga       685
Gly Leu Glu Ser Ala Glu Val Glu Ala Leu Lys Asn Leu Pro Asp Gly
        115                 120                 125 aaa att ggc gat gca atg aat caa ctc agc ccg gaa tac cgg atg gtg       733
Lys Ile Gly Asp Ala Met Asn Gln Leu Ser Pro Glu Tyr Arg Met Val
    130                 135                 140 gtt tat tat gcc gat gta gaa gat ctc gca tac aaa gaa atc gcc gag       781
Val Tyr Tyr Ala Asp Val Glu Asp Leu Ala Tyr Lys Glu Ile Ala Glu
145                 150                 155                 160 atc atg gac gtt cca ctc gga act gtg atg tcc cga ctc cat cgt gga       829
Ile Met Asp Val Pro Leu Gly Thr Val Met Ser Arg Leu His Arg Gly
                165                 170                 175 aga aaa cag ctc cga gga atg tta aag gaa gta gcg aag gaa caa ggc       877
Arg Lys Gln Leu Arg Gly Met Leu Lys Glu Val Ala Lys Glu Gln Gly
            180                 185                 190 att ggt ctt gaa cat ccc gac atg aag aaa aat tcg gag gca               919
Ile Gly Leu Glu His Pro Asp Met Lys Lys Asn Ser Glu Ala
        195                 200                 205 taacgatgac gaatctcaac cgcagcgact cgcaaggtga ttgtggctgc cctgaattct     979
tcgatgaaat gtatcagcta ctcgacgatc aactcagcga gtccgcctgc gagcgtctgc    1039
ggattcacgc ggcaggctgc ccggcatgcc agcaactgct agaggccgaa tcggagtttc    1099
gtagtctgtt gcgcaagtgc tgctgcgaat cggcacctgt ggagctccg               1148
```

```
<210> SEQ ID NO 2
<211> LENGTH: 206
<212> TYPE: PRT
<213> ORGANISM: Corynebacterium glutamicum

<400> SEQUENCE: 2

Met Ala Glu Asn Arg Thr Gly Thr Val Asp Gly Asp Ala Leu Ala Ala
1               5                  10                 15

Arg Phe Glu Glu Glu Ala Leu Pro Leu Leu Asp Gln Leu Tyr Gly Gly
            20                  25                  30

Ala Leu Arg Met Thr Arg Asn Pro Ala Asp Ala Glu Asp Leu Val Gln
        35                  40                  45

Asp Thr Tyr Ile Lys Ala Tyr Gln Ala Phe Ala Ser Phe Lys Pro Gly
    50                  55                  60

Thr Asn Leu Lys Ala Trp Leu Tyr Arg Ile Met Thr Asn Thr Tyr Ile
65                  70                  75                  80

Asn Met Tyr Arg Lys Lys Gln Arg Gln Pro Ser Gln Thr Ser Ala Asp
                85                  90                  95

Glu Ile Thr Asp Tyr Gln Leu Val Glu Ser Gln Ser His Thr Ser Thr
            100                 105                 110

Gly Leu Glu Ser Ala Glu Val Glu Ala Leu Lys Asn Leu Pro Asp Gly
        115                 120                 125

Lys Ile Gly Asp Ala Met Asn Gln Leu Ser Pro Glu Tyr Arg Met Val
    130                 135                 140

Val Tyr Tyr Ala Asp Val Glu Asp Leu Ala Tyr Lys Glu Ile Ala Glu
145                 150                 155                 160

Ile Met Asp Val Pro Leu Gly Thr Val Met Ser Arg Leu His Arg Gly
                165                 170                 175

Arg Lys Gln Leu Arg Gly Met Leu Lys Glu Val Ala Lys Glu Gln Gly
            180                 185                 190

Ile Gly Leu Glu His Pro Asp Met Lys Lys Asn Ser Glu Ala
        195                 200                 205

<210> SEQ ID NO 3
<211> LENGTH: 28
<212> TYPE: DNA
<213> ORGANISM: Corynebacterium glutamicum

<400> SEQUENCE: 3 caggtaccctt ttcgaaaggg gccacatg                                28

<210> SEQ ID NO 4
<211> LENGTH: 28
<212> TYPE: DNA
<213> ORGANISM: Corynebacterium glutamicum

<400> SEQUENCE: 4
tgtctagaaa gaattcaggg cagccaca                                 28
```

NUCLEOTIDE SEQUENCES WHICH CODE FOR THE SIGH GENE

BACKGROUND OF THE INVENTION

The invention provides nucleotide sequences from coryneform bacteria which code for the sigH gene and a process for the fermentative preparation of amino acids using bacteria in which the sigH gene is enhanced. All references cited herein are expressly incorporated by reference. Incorporation by reference is also designated by the term "I.B.R." following any citation.

L-Amino acids are used in human medicine and in the pharmaceuticals industry, in the foodstuffs industry and especially in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and produce amino acids are obtained in this manner.

Methods of the recombinant DNA technique have also been employed for some years for improving the strain of Corynebacterium strains which produce L-amino acid, by amplifying individual amino acid biosynthesis genes and investigating the effect on the amino acid production.

The invention providing new measures for improved fermentative preparation of amino acids.

BRIEF SUMMARY OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. Lysine is particularly preferred.

The invention provides an isolated polynucleotide from coryneform bacteria, comprising a polynucleotide sequence which codes for the sigH gene, chosen from the group consisting of
a) polynucleotide which is identical to the extent of at least 70% to a polynucleotide which codes for a polypeptide which comprises the amino acid sequence of SEQ ID No. 2,
b) polynucleotide which codes for a polypeptide which comprises an amino acid sequence which is identical to the extent of at least 70% to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c), the polypeptide preferably having the activity of sigma factor H.

The invention also provides the above-mentioned polynucleotide, this preferably being a DNA which is capable of replication, comprising:
(i) the nucleotide sequence shown in SEQ ID No. 1, or
(ii) at least one sequence which corresponds to sequence (i) within the range of the degeneration of the genetic code, or
(iii) at least one sequence which hybridizes with the sequence complementary to sequence (i) or (ii), and optionally
(iv) sense mutations of neutral function in (i).

The invention also provides
a polynucleotide, in particular DNA, which is capable of replication and comprises the nucleotide sequence as shown in SEQ ID No. 1;
a polynucleotide which codes for a polypeptide which comprises the amino acid sequence as shown in SEQ ID No. 2;
a vector containing the polynucleotide according to the invention, in particular a shuttle vector or plasmid vector, and
coryneform bacteria which contain the vector or in which the sigH gene is enhanced.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID No. 1 or a fragment thereof, and isolation of the polynucleotide sequence mentioned.

BRIEF DESCRIPTION OF THE FIGURE

FIG. 1: Map of the plasmid pEC-XK99E

FIG. 2: Map of the plasmid pEC-XK99EsigHalex.

The abbreviations and designations used have the following meaning:

| | |
|---|---|
| Kan: | Kanamycin resistance gene aph(3')-IIa from *Escherichia coli* |
| HindIII | Cleavage site of the restriction enzyme HindIII |
| XbaI | Cleavage site of the restriction enzyme XbaI |
| KpnI | Cleavage site of the restriction enzyme KpnI |
| Ptrc | Trc promoter |
| T1 | Termination region T1 |
| T2 | Termination region T2 |
| Per | Replication effector per |
| Rep | Replication region rep of the plasmid pGA1 |
| LacIq | LacIq repressor of the lac operon of *Escherichia coli* |
| Sigh | Cloned sigHgene |

DETAILED DESCRIPTION OF THE INVENTION

Polynucleotides which comprise the sequences according to the invention are suitable as hybridization probes for RNA, cDNA and DNA, in order to isolate, in the full length, nucleic acids or polynucleotides or genes which code for sigma factor H or to isolate those nucleic acids or polynucleotides or genes which have a high similarity of sequence with that of the sigH gene. They are also suitable for incorporation into so-called "arrays", "micro arrays" or "DNA chips" in order to detect and determine the corresponding polynucleotides.

Polynucleotides which comprise the sequences according to the invention are furthermore suitable as primers with the aid of which DNA of genes which code for sigma factor H can be prepared by the polymerase chain reaction (PCR)

Such oligonucleotides which serve as probes or primers comprise at least 25, 26, 27, 28, 29 or 30, preferably at least 20, 21, 22, 23 or 24, very particularly preferably at least 15, 16, 17, 18 or 19 successive nucleotides. Oligonucleotides which have a length of at least 31, 32, 33, 34, 35, 36, 37, 38, 39 or 40, or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70% to 80%, preferably at least 81% to 85%, particularly preferably at least 86% to 90%, and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of sigma factor H and also those which are at least 70% to 80%, preferably at least 81% to 85%, particularly preferably at least 86% to 90%, and very particularly preferably at least 91%, 93%, 95%, 97% or 99% identical to the polypeptide according to SEQ ID No. 2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences which code for the sigH gene are enhanced, in particular over-expressed.

The term "enhancement" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The microorganisms which the present invention provides can produce L-amino acids from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum*, which is known among experts for its ability to produce L-amino acids.

Suitable strains of the genus Corynebacterium, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-amino acid-producing mutants or strains prepared therefrom.

The inventors have succeeded in isolating the new sigH gene of *C. glutamicum* which codes for the enzyme sigma factor H.

To isolate the sigH gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) I.B.R., or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495–508 (1987)) I.B.R. Bathe et al. (Molecular and General Genetics, 252:255–265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160–2164 I.B.R.) in the *E. coli* K-12 strain NM554 (Raleigh et al., 1988, Nucleic Acids Research 16:1563–1575 I.B.R.).

Börmann et al. (Molecular Microbiology 6(3), 317–326) (1992)) I.B.R. in turn describe a gene library of *C. glutamicum* ATCC13032 using the cosmid pHC79 (Hohn and Collins, Gene 11, 291–298 (1980) I.B.R.).

To prepare a gene library of *C. glutamicum* in *E. coli* it is also possible to use plasmids such as pBR322 (Bolivar, Life Sciences, 25, 807–818 (1979) I.B.R.) or pUC9 (Vieira et al., 1982, Gene, 19:259–268 I.B.R.). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649) I.B.R. The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977) I.B.R.

The resulting DNA sequences can then be investigated with known algorithms or sequence analysis programs, such as e.g. that of Staden (Nucleic Acids Research 14, 217–232 (1986)) I.B.R., that of Marck (Nucleic Acids Research 16, 1829–1836 (1988)) I.B.R. or the GCG program of Butler (Methods of Biochemical Analysis 39, 74–97 (1998)) I.B.R.

The new DNA sequence of *C. glutamicum* which codes for the sigH gene and which, as SEQ ID No. 1, is a constituent of the present invention has been obtained in this manner. The amino acid sequence of the corresponding protein has furthermore been derived from the present DNA sequence by the methods described above. The resulting amino acid sequence of the sigH gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255–260) I.B.R. The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996 I.B.R.).

A 5×SSC buffer at a temperature of approx. 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995 I.B.R.) a temperature of approx. 50–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50 to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) I.B.R. and in Newton and Graham: PCR (Spektrum Akademischer Verlag, Heidelberg, Germany, 1994) I.B.R.

In the work on the present invention, it has been found that coryneform bacteria produce amino acids in an improved manner after over-expression of the sigH gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative amino acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)) I.B.R., in Guerrero et al. (Gene 138, 35–41 (1994)) I.B.R., Tsuchiya and Morinaga (Bio/Technology 6, 428–430 (1988)) I.B.R., in Eikmanns et al. (Gene 102, 93–98 (1991)) I.B.R., in EP 0 472 869 I.B.R., in U.S. Pat. No. 4,601,893 I.B.R., in Schwarzer and Pühler (Bio/Technology 9, 84–87 (1991) I.B.R., in Reinscheid et al. (Applied and Environmental Microbiology 60, 126–132 (1994)) I.B.R., in LaBarre et al. (Journal of Bacteriology 175, 1001–1007 (1993)) I.B.R., in WO 96/15246 I.B.R., in Malumbres et al. (Gene 134, 15–24 (1993)) I.B.R., in JP-A-10-229891 I.B.R., in Jensen and Hammer (Biotechnology and Bioengineering 58, 191–195 (1998)) I.B.R., in Makrides (Microbiological Reviews 60:512–538 (1996)) I.B.R. and in known textbooks of genetics and molecular biology.

By way of example, for enhancement the sigH gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549–554 I.B.R.), pEKEx1 (Eikmanns et al., Gene 102:93–98 (1991) I.B.R.) or pHS2-1 (Sonnen et al., Gene 107:69–74 (1991) I.B.R.) are based on the cryptic plasmids pHM1519, pBL1 or pGA1. Other plasmid vectors, such as e.g. those based on pCG4 (U.S. Pat. No. 4,489,160 I.B.R.), or pNG2 (Serwold-Davis et al., FEMS Microbiology Letters 66, 119–124 (1990) I.B.R.), or pAG1 (U.S. Pat. No. 5,158,891 I.B.R.), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) I.B.R. for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983) I.B.R.), pK18mob or pK19mob (Schafer et al., Gene 145, 69–73 (1994) I.B.R.), PGEM-T (Promega corporation, Madison, Wis., USA), pCR2.1-TOPO (Shuman (1994). Journal of Biological Chemistry 269:32678–84 I.B.R.; U.S. Pat. No. 5,487,993 I.B.R.), pCR®Blunt (Invitrogen, Groningen, Holland; Bernard et al., Journal of Molecular Biology, 234: 534–541 (1993) I.B.R.), pEM1 (Schrumpf et al, 1991, Journal of Bacteriology 173:4510–4516 I.B.R.) or pBGS8 (Spratt et al., 1986, Gene 41: 337–342 I.B.R.). The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756–759 (1994) I.B.R.). Methods for transformation are described, for example, by Thierbach et al. (Applied Microbiology and Biotechnology 29, 356–362 (1988) I.B.R.), Dunican and Shivnan (Bio/Technology 7, 1067–1070 (1989) I.B.R.) and Tauch et al. (FEMS Microbiological Letters 123, 343–347 (1994) I.B.R.). After homologous recombination by means of a "cross over" event, the resulting strain contains at least two copies of the gene in question.

In addition, it may be advantageous for the production of L-amino acids to enhance, in particular over-express one or more enzymes of the particular biosynthesis pathway, of glycolysis, of anaplerosis, of the citric acid cycle, of the pentose phosphate cycle, of amino acid export and optionally regulatory proteins, in addition to the sigH gene.

Thus, for example, for the preparation of L-amino acids, in addition to enhancement of the sigH gene, one or more genes chosen from the group consisting of
the dapA gene which codes for dihydrodipicolinate synthase (EP-B 0 197 335 I.B.R.),
the gap gene which codes for glyceraldehyde 3-phosphate dehydrogenase (Eikmanns (1992), Journal of Bacteriology 174:6076–6086 I.B.R.),
the tpi gene which codes for triose phosphate isomerase (Eikmanns (1992), Journal of Bacteriology 174:6076–6086 I.B.R.),
the pgk gene which codes for 3-phosphoglycerate kinase (Eikmanns (1992), Journal of Bacteriology 174:6076–6086
the zwf gene which codes for glucose 6-phosphate dehydrogenase (JP-A-09224661 I.B.R.),
the pyc gene which codes for pyruvate carboxylase (DE-A-198 31 609 I.B.R.),
the mqo gene which codes for malate-quinone oxidoreductase (Molenaar et al., European Journal of Biochemistry 254, 395–403 (1998) I.B.R.),
the lysC gene which codes for a feed-back resistant aspartate kinase (Accession No.P26512; EP-B-0387527; EP-A-0699759 I.B.R.),
the lysE gene which codes for lysine export (DE-A-195 48 222 I.B.R.),
the hom gene which codes for homoserine dehydrogenase (EP-A 0131171 I.B.R.),
the ilvA gene which codes for threonine dehydratase (Mockel et al., Journal of Bacteriology (1992) 8065–8072) I.B.R.) or the ilvA(Fbr) allele which codes for a "feed back resistant" threonine dehydratase (Möckel et al., (1994) Molecular Microbiology 13: 833–842 I.B.R.),
the ilvBN gene which codes for acetohydroxy-acid synthase (EP-B 0356739 I.B.R.),
the ilvD gene which codes for dihydroxy-acid dehydratase (Sahm and Eggeling (1999) Applied and Environmental Microbiology 65: 1973–1979 I.B.R.),
the zwa1 gene which codes for the Zwa1 protein (DE: 19959328.0 I.B.R., DSM 13115)
can be enhanced, in particular over-expressed.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

It may furthermore be advantageous for the production of L-amino acids, in addition to the enhancement of the sigH gene, for one or more of the genes chosen from the group consisting of:
the pck gene which codes for phosphoenol pyruvate carboxykinase (DE 199 50 409.1 I.B.R.; DSM 13047),
the pgi gene which codes for glucose 6-phosphate isomerase (U.S. Ser. No. 09/396,478 I.B.R.; DSM 12969),
the poxB gene which codes for pyruvate oxidase (DE: 1995 1975.7 I.B.R.; DSM 13114),
the zwa2 gene which codes for the Zwa2 protein (DE: 19959327.2 I.B.R., DSM 13113)
to be attenuated, in particular for the expression thereof to be reduced.

In addition to over-expression of the sigH gene it may furthermore be advantageous for the production of amino acids to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982 I.B.R.).

The invention also provides the microorganisms prepared according to the invention, and these can be cultured continuously or discontinuously in the batch process (batch culture) or in the fed batch (feed process) or repeated fed batch process (repetitive feed process) for the purpose of production of amino acids. A summary of known culture methods is described in the textbook by Chmiel (Bioprozesstechnik 1. Einfuhrung in die Bioverfahrenstechnik [Bioprocess Technology 1. Introduction to Bioprocess Technology (Gustav Fischer Verlag, Stuttgart, 1991) I.B.R.) or in the textbook by Storhas (Bioreaktoren und periphere Einrichtungen [Bioreactors and Peripheral Equipment] (Vieweg Verlag, Braunschweig/Wiesbaden, 1994) I.B.R.).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R.

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) I.B.R. by ion exchange chromatography with subsequent ninhydrin derivation, or it can be carried out by reversed phase HPLC, for example as described by Lindroth et al. (Analytical Chemistry (1979) 51: 1167–1174) I.B.R.

The process according to the invention is used for fermentative preparation of amino acids.

The following microorganisms have been deposited as a pure culture at the Deutsche Sammlung für Mikroorganismen und Zellkulturen (DSMZ=German Collection of Microorganisms and Cell Cultures, Braunschweig, Germany) in accordance with the Budapest Treaty:

*Escherichia coli* DH5αmcr/pEC-XK99EsigHa1ex as DSM 14374 on Jun. 29, 2001

*Corynebacterium glutamicum* DSM5715/pEC-XK99E as DSM13455 on Apr. 17, 2000.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbor Laboratory Press, Cold Spring Harbor, N.Y., USA I.B.R.). Methods for transformation of *Escherichia coli* are also described in this handbook.

The composition of the usual nutrient media, such as LB or TY medium, can also be found in the handbook by Sambrook et al.

EXAMPLE 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179 I.B.R.) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector Super-Cos1 (Wahl et al. (1987) Proceedings of the National Academy of Sciences USA 84:2160–2164 I.B.R.), obtained from Stratagene (La Jolla, USA, Product Description Super-Cos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575 I.B.R.) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor I.B.R.), the cells being plated out on LB agar (Lennox, 1955, Virology, 1:190 I.B.R.) with 100 mg/l ampicillin. After incubation overnight at 37° C., recombinant individual clones were selected.

EXAMPLE 2

Isolation and Sequencing of the sigH Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor) I.B.R., the DNA mixture being incubated overnight with T4 ligase (Pharmacia Biotech, Freiburg, Germany). This ligation mixture was then electroporated (Tauch et al. 1994, FEMS Microbiol Letters, 123:343–7 I.B.R.) into the *E. coli* strain DH5αMCR (Grant, 1990, Proceedings of the National Academy of Sciences U.S.A., 87:4645–4649 I.B.R.) and plated out on LB agar (Lennox, 1955, Virology, 1:190 I.B.R.) with 50 mg/l zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) I.B.R. with modifications according to Zimmermann et al. (1990, Nucleic Acids Research, 18:1067) I.B.R. The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231 I.B.R.) version 97-0. The individual sequences of the pZero1 derivatives were assembled to a continuous contig. The computer-assisted coding region analysis was prepared with the XNIP program (Staden, 1986, Nucleic Acids Research, 14:217–231 I.B.R.).

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) I.B.R. and by Steinberg, Michael "Protein Structure Prediction" (A Practical Approach), Oxford Univ. Press, Inc. (1997) I.B.R.

The resulting nucleotide sequence is shown in SEQ ID No. 1. Analysis of the nucleotide sequence showed an open reading frame of 621 base pairs, which was called the sigH gene. The sigH gene codes for a protein of 206 amino acids.

EXAMPLE 3
Preparation of the Shuttle Expression Vector pEC-XK99EsigHalex for Enhancement of the sigH Gene in *C. glutamicum*

3.1 Cloning of the sigH Gene

From the strain ATCC 13032, chromosomal DNA was isolated by the method of Eikmanns et al. (Microbiology 140: 1817–1828 (1994)) I.B.R. On the basis of the sequence of the sigH gene known for *C. glutamicum* from example 2, the following oligonucleotides were chosen for the polymerase chain reaction (see SEQ ID No. 3 and SEQ ID No. 4):

restriction endonuclease XbaI, which are marked by underlining in the nucleotide sequence shown above.

The sigH fragment 712 bp in size was cleaved with the restriction endonucleases Kpn1 and XbaI and then isolated from the agarose gel with the QiaExII Gel Extraction Kit (Product No. 20021, Qiagen, Hilden, Germany).

3.2 Construction of the Shuttle Vector pEC-XK99E

The *E. coli-C. glutamicum* shuttle vector pEC-XK99E was constructed according to the prior art. The vector contains the replication region rep of the plasmid pGA1 including the replication effector per (U.S. Pat. No. 5,175, 108 I.B.R.; Nesvera et al., Journal of Bacteriology 179, 1525–1532 (1997) I.B.R.), the kanamycin resistance gene aph(3')-IIa from *Escherichia coli* (Beck et al. (1982), Gene 19: 327–336 I.B.R.), the replication origin of the trc promoter, the termination regions T1 and T2, the laqI$^q$ gene (repressor of the lac operon of *E. coli*) and a multiple cloning site (mcs) (Norrander, J. M. et al. Gene 26, 101–106 (1983) I.B.R.) of the plasmid pTRC99A (Amann et al. (1988), Gene 69: 301–315 I.B.R.).

The trc promoter can be induced by addition of the lactose derivative IPTG (isopropyl β-D-thiogalactopyranoside).

The *E. coli-C. glutamicum* shuttle vector pEC-XK99E constructed was transferred into *C. glutamicum* DSM5715 by means of electroporation (Liebl et al., 1989, FEMS Microbiology Letters, 53:299–303 I.B.R.). Selection of the transformants took place on LBHIS agar comprising 18.5 g/l brain-heart infusion broth, 0.5 M sorbitol, 5 g/l Bactotryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology, 144, 915–927 I.B.R.), cleaved with the restriction endonuclease HindIII, and the plasmid was checked by subsequent agarose gel electrophoresis.

The plasmid construct obtained in this way was called pEC-XK99E (FIG. 1). The strain obtained by electroporation of the plasmid pEC-XK99E in the *C.glutamicum* strain DSM5715 was called DSM5715/pEC-XK99E and deposited as DSM13455 at the Deutsche Sammlung für Mikroorganismen und Zellkulturen (DSMZ=German Collection of Microorganisms and Cell Cultures, Braunschweig, Germany) in accordance with the Budapest Treaty.

3.3 Cloning of sigH in the *E. coli-C. glutamicum* Shuttle Vector pEC-XK99E

The *E. coli-C. glutamicum* shuttle vector pEC-XK99E described in example 3.2 was used as the vector. DNA of this

```
sigHex1:
5' ca ggt acc-ttt tcg aaa ggg gcc aca tg 3'      SEQ ID NO:3 sigHex2:
5' tg tct aga-aag aat tca ggg cag cca ca 3       SEQ ID NO:4'
```

The primers shown were synthesized by MWG-Biotech AG (Ebersberg, Germany) and the PCR reaction was carried out by the standard PCR method of Innis et al. (PCR protocols. A guide to methods and applications, 1990, Academic Press) I.B.R. with Pwo-Polymerase from Roche Diagnostics GmbH (Mannheim, Germany). With the aid of the polymerase chain reaction, the primers allow amplification of a DNA fragment 712 bp in size, which carries the sigH gene. Furthermore, the primer sigHex1 contains the sequence for the cleavage site of the restriction endonuclease Kpn1, and the primer sigHex2 the cleavage site of the plasmid was cleaved completely with the restriction enzymes KpnI and XbaI and then dephosphorylated with shrimp alkaline phosphatase (Roche Diagnostics GmbH, Mannheim, Germany, Product Description SAP, Product No. 1758250).

The sigH fragment approx. 700 bp in size described in example 3.1, obtained by means of PCR and cleaved with the restriction endonucleases KpnI and XbaI, was mixed with the prepared vector pEC-XK99E and the batch was treated with T4 DNA ligase (Amersham Pharmacia, Freiburg, Germany, Product Description T4-DNA-Ligase, Code no.27-0870-04). The ligation batch was transformed in the *E. coli* strain DH5αmcr (Hanahan, In: DNA cloning. A practical approach. Vol. I. IRL-Press, Oxford, Washington D.C., USA I.B.R.). Selection of plasmid-carrying cells was made by plating out the transformation batch on LB agar (Lennox, 1955, Virology, 1:190 I.B.R.) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzymes XbaI and KpnI to check the plasmid by subsequent agarose gel electrophoresis. The resulting plasmid was called pEC-XK99EsigHalex. It is shown in FIG. 2.

EXAMPLE 4
Transformation of the Strain DSM5715 with the Plasmid pEC-XK99EsigHalex1

The strain DSM5715 was transformed with the plasmid pEC-XK99EsigHalex using the electroporation method described by Liebl et al., (FEMS Microbiology Letters, 53:299–303 (1989) I.B.R.). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology, 144, 915–927 I.B.R.), cleaved with the restriction endonucleases XbaI and KpnI, and the plasmid was checked by subsequent agarose gel electrophoresis. The strain obtained was called DSM5715/pEC-XK99EsigHalex.

EXAMPLE 5
Preparation of Lysine

The *C. glutamicum* strain DSM5715/pEC-XK99EsigHalex obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l)) for 24 hours at 33° C. Starting from this agar plate culture, a preculture was seeded (10 ml medium in a 100 ml conical flask). The complete medium CgIII was used as the medium for the preculture.

|  | Medium Cg III |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1. Medium MM was used for the main culture.

|  | medium MM |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing is carried out in a 10 ml volume in a 100 ml conical flask with baffles. Kanamycin (25 mg/l) and IPTG (1 mM/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivation with ninhydrin detection.

The result of the experiment is shown in table 1.

TABLE 1

| Strain | OD (660 nm) | Lysine HCl g/l |
|---|---|---|
| DSM5715 | 6.9 | 13.6 |
| DSM5715/pEC-XK99EsigHalex | 10.0 | 14.25 |

This application claims priority to German Priority Document Application No. 100 43 333.2, filed on Sep. 2, 2000 and to German Priority Document Application No. 101 33 427.3, filed on Jul. 10, 2001. Both German Priority Documents are hereby incorporated by reference in their entirety.

We claim:

1. A transformed Coryneform bacterium comprising an isolated sigH gene having the polynucleotide sequence of SEQ ID NO: 1.

2. The bacterium of claim 1, wherein said sigH gene is over-expressed.

3. A transformed recombinant coryneform bacterium comprising an increased intracellular concentration of polypeptide having the amino acid sequence of SEQ ID NO: 2, wherein said intracellular concentration is increased by at least 10% over a concentration of a wild type coryneform bacterium.

4. The coryneform bacterium of claim 3, wherein said intracellular concentration is increased by at least 25% over the concentration of a wild type coryneform bacterium.

5. The coryneform bacterium of claim 3, wherein said intracellular concentration is increased by at least 50% over the concentration of a wild type coryneform bacterium.

6. The coryneform bacterium of claim 3, wherein said polypeptide is encoded by an isolated polynucleotide comprising the nucleotide sequence of SEQ ID NO: 1 and said polypeptide is over-expressed.

7. The coryneform bacterium of claim 6, wherein said isolated polynucleotide comprises nucleotides 302 to 919 of SEQ ID NO: 1.

8. A transformed coryneform bacterium comprising an isolated polynucleotide encoding a polypeptide comprising the amino acid sequence of SEQ ID NO: 2.

9. The coryneform bacterium of claim 8, wherein said polypeptide is over-expressed to the extent that an intracellular concentration of said polypeptide is increased by at least 10% over a concentration in a wild type coryneform bacterium.

10. The coryneform bacterium of claim 9, wherein said over-expression of said polypeptide is achieved by increasing the copy number of the polynucleotide encoding said polypeptide.

11. The coryneform bacterium of claim 2, wherein said coryneform bacterium is selected from the group consisting of *Corynebacterium glutamicum, Corynebacterium acetoglutamicum, Corynebacterium acetoacidophilum, Corynebacterium thermoaminogenes, Corynebacterium melassecola, Brevibacterium flavum, Brevibacterium lactofermentum,* and *Brevibacterium divaricatum*.

12. The coryneform bacterium of claim 8, wherein said coryneform bacterium is selected from the group consisting of *Corynebacterium glutamicum, Corynebacterium acetoglutamicum, Corynebacterium acetoacidophilum, Corynebacterium thermoaminogenes, Corynebacterium melassecola, Brevibacterium flavum, Brevibacterium lactofermentum,* and *Brevibacterium divaricatum*.

13. The coryneform bacterium of claim 3, wherein said coryneform bacterium produces an L-amino acid selected from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

14. The coryneform bacterium of claim 13, wherein said L-amino acid is L-lysine.

15. The coryneform bacterium of claim 4, wherein said coryneform bacterium produces an L-amino acid selected from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

16. The coryneform bacterium of claim 15, wherein said L-amino acid is L-lysine.

17. The coryneform bacterium of claim 11, wherein said coryneform bacterium produces an L-amino acid selected from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

18. The coryneform bacterium of claim 17, wherein said L-amino acid is L-lysine.

\* \* \* \* \*